US012241056B2

(12) United States Patent
Lee

(10) Patent No.: US 12,241,056 B2
(45) Date of Patent: Mar. 4, 2025

(54) METHOD FOR EXTENDING TELOMERE OF CELL

(71) Applicant: STEMON INC., Seongnam-si (KR)

(72) Inventor: Yong Seung Lee, Suwon-si (KR)

(73) Assignee: STEMON INC., Seongnam-si (KR)

( * ) Notice: Subject to any disclaimer, the term of this patent is extended or adjusted under 35 U.S.C. 154(b) by 876 days.

(21) Appl. No.: 17/276,201

(22) PCT Filed: Sep. 10, 2019

(86) PCT No.: PCT/KR2019/011681
§ 371 (c)(1),
(2) Date: Mar. 15, 2021

(87) PCT Pub. No.: WO2020/071652
PCT Pub. Date: Apr. 9, 2020

(65) Prior Publication Data

US 2022/0025352 A1 Jan. 27, 2022

(30) Foreign Application Priority Data

Oct. 2, 2018 (KR) ........................ 10-2018-0117265
Sep. 3, 2019 (KR) ........................ 10-2019-0108764

(51) Int. Cl.
*C12N 13/00* (2006.01)
*C12N 5/071* (2010.01)
*C12N 5/074* (2010.01)
*C12N 5/077* (2010.01)
*C12N 5/0775* (2010.01)
*C12N 5/09* (2010.01)

(52) U.S. Cl.
CPC .......... *C12N 13/00* (2013.01); *C12N 5/0625* (2013.01); *C12N 5/0653* (2013.01); *C12N 5/0656* (2013.01); *C12N 5/0667* (2013.01); *C12N 5/0693* (2013.01); *C12N 5/0696* (2013.01); *C12N 2521/10* (2013.01); *C12N 2523/00* (2013.01); *C12N 2529/10* (2013.01)

(58) Field of Classification Search
CPC .... C12N 13/00; C12N 5/0625; C12N 5/0653; C12N 5/0656; C12N 5/0667; C12N 5/0693; C12N 5/0696
See application file for complete search history.

(56) References Cited

U.S. PATENT DOCUMENTS

2004/0082074 A1* 4/2004 McGrath ................ G09B 23/20 436/171
2014/0242155 A1 8/2014 Blau et al.
2018/0280413 A1 10/2018 Fauce et al.

FOREIGN PATENT DOCUMENTS

EP 2959005 A1 12/2015
KR 10-1855967 B1 5/2018
KR 10-2018-0123512 A 11/2018
WO 95/13383 A1 5/1995
WO WO-2016000075 A1 * 1/2016 .............. A61N 2/02

OTHER PUBLICATIONS

Forýtková, L et al. "Effect of ultrasound on DNA synthesis in tumor cells." Ultrasound in medicine & biology vol. 21,4 (1995): 585-92. (Year: 1995).*
Koskas, Sivan, et al. "Heat shock factor 1 promotes Terra transcription and telomere protection upon heat stress." Nucleic acids research 45.11 (2017): 6321-6333. (Year: 2017).*
Maeda, Toyoki et al. "Alterations in the telomere length distribution and the subtelomeric methylation status in human vascular endothelial cells under elevated temperature in culture condition." Aging clinical and experimental research vol. 25,3 (2013): 231-8. (Year: 2013).*
Khavinson, V. Kh, I. E. Bondarev, and A. A. Butyugov. "Epithalon peptide induces telomerase activity and telomere elongation in human somatic cells." Bulletin of Experimental Biology and Medicine 135.6 (2003): 590-592. (Year: 2003).*
Romano, Gal Hagit, et al. "Environmental stresses disrupt telomere length homeostasis." PLoS genetics 9.9 (2013): e1003721. (Year: 2013).*
Lieb, E.H., Yngvason, J., Physics Reports 310 (1999) 1-96. (Year: 1999).*
Wenzel, Dirk, Francesca Palladino, and Monika Jedrusik-Bode. "Epigenetics in C. elegans: facts and challenges." genesis 49.8 (2011): 647-661. (Year: 2011).*
Hernandez-Caballero, E., et al. "Role of telomere length in subtelomeric gene expression and its possible relation to cellular senescence." BMB reports 42.11 (2009): 747-751. (Year: 2009).*

(Continued)

*Primary Examiner* — Ekaterina Poliakova-Georgantas
*Assistant Examiner* — John Charles McKillop
(74) *Attorney, Agent, or Firm* — Bridgeway IP Law Group, PLLC; Jihun Kim

(57) ABSTRACT

A method for elongating telomeres of cells comprises steps of: providing physical stimulation directly or indirectly to cells; and culturing a mixture of the cells and a medium for a predetermined time, wherein providing the stimulation directly to the cells comprises applying physical stimulation to the medium containing the cells, and providing the stimulation indirectly to the cells comprises applying physical stimulation to the medium not containing the cells and then mixing the medium and the cells. The method for elongating telomeres of cells is simpler than a conventional method and is superior in terms of time, cost, efficiency, and safety. In addition, the method induces cell division and provides an anti-aging effect, in addition to simply elongating telomeres. Thereby, it is expected that the method can ameliorate and prevent not only problems caused by shortening of telomeres, but also various aging-related diseases and conditions.

6 Claims, 15 Drawing Sheets

(56) References Cited

OTHER PUBLICATIONS

Murillo-Ortiz, B. et al., "Increased telomere length and proliferative potential in peripheral blood mononuclear cells of adults of different ages stimulated with concanavalin A", BMC Geriatrics, 2013, 13:99, pp. 1-5.

Khavinson, V. K. et al., "Epithalon peptide induces telomerase activity and telomere elongation in human somatic cells", Bulletin of Experimental Biology and Medicine, Jun. 2003, vol. 135, No. 6, pp. 590-592.

* cited by examiner

METHOD FOR EXTENDING TELOMERE OF CELL

TECHNICAL FIELD

The present invention relates to a method for elongating telomeres of cells, and more particularly, to a method of elongating telomeres of cells by providing physical stimulation directly or indirectly to the cells, and cells having telomeres elongated by the method.

BACKGROUND ART

Telomeres are DNA repeat structures (TTAGGG in humans) at both ends of chromosomes. Telomeres bind to the shelterin complex to form a protective cap, which regulates the multiplication ability of cells and prevents binding between chromosomes and loss of genetic information during cell division. Since DNA polymerase cannot completely amplify the 3' end, telomeres are shortened by 30 to 200 bp for each cell division. When telomeres become shorter than the threshold value and become closer to the coding DNA and the loop structure of the telomeres cannot be maintained, the exposed telomeres are recognized by the p53 or p16INK4a signaling pathways, so that cell division stops and the cells die due to senescence.

Telomeres may be elongated by the reverse transcriptase telomerase, and the human telomerase complex is composed of TERC, which is an RNA molecule that acts as a template for telomere synthesis, PERT, which is a catalytic subunit, and telomerase-associated proteins such as DKC1 and TEP1. In normal cases, somatic cells have little telomerase activity, and high telomerase activity is detected only in stem cells and progenitor cells that require active division ability.

When the division of multiple cells is stopped as the telomeres are shortened, various problems may arise, and in particular, various symptoms represented by aging and degeneration may arise. It was already known that diseases that cause problems in the regeneration of bone marrow cells, such as congenital dyskeratosis congenita in which skin tissue is degenerated, and aplastic anemia in which blood cells counts are low, arise due to abnormalities in telomeres maintenance, such as mutations in telomerase or Shelterin complex-related genes containing the same. In recent years, studies have been reported that telomeres in patients suffering from aging-related diseases such as hypertension, metabolic syndrome, diabetes, and dementia are shorter than those in normal people, and thus studies on the possibility of slowing aging by increasing the length of telomeres have attracted attention. In addition, it has been shown that regenerative activities can be actively performed by increasing telomerase activity in somatic cells, which are generally known to have little telomerase activity. In particular, it has been reported that the increase in telomerase activity is effective when it is necessary to supplement various tissues such as the myocardium, liver, cornea, skin, blood vessels, cartilage and bone, immune cells, blood cells, etc. due to burns, injuries, aging and diseases. However, studies have also been reported that a number of cancer cells occurred in mice in which a gene capable of extending the length of telomeres was continuously overexpressed, suggesting that long telomeres become a risk factor for cancer. Therefore, it can be expected that, if telomeres can be temporarily elongated, this telomere elongation can alleviate various symptoms associated with aging and degeneration without the risk of cancer development, and can be particularly useful in the field of regenerative medicine.

According to the various utilities expected as described above, various methods for elongating telomeres have been developed. US Patent Application Publication No. 2018-0280413 discloses a pharmaceutical composition containing a compound for enhancing telomerase activity. However, in this case, a process of synthesizing the compound is required, and the time for the composition to exhibit the effect thereof is long. In addition, the effect of this compound has been shown to last for a considerable amount of time, but it is known that there is a risk of cancer development if the telomerase activity is continuously high. European Patent Publication No. 2959005 discloses a nucleic acid encoding telomerase. In this case, a synthesis process is also required, and since the nucleic acid is hydrophilic, a delivery vehicle is additionally required to deliver the nucleic acid into cells. Korean Patent Application Publication No. 10-2018-0123512 discloses a telomerase-derived peptide. In this case, a synthesis process is also required, and this peptide exhibits an effect when measured 1 month after injection 3 times a week for 2 months, and thus can be cumbersome and costly. Therefore, there is a need for a method for elongating telomeres, which is more reasonable in terms of cost and time of synthesis, etc., and is safe and more efficient.

DISCLOSURE

Technical Problem

The present invention has been made in order to solve the above-described problems, and one embodiment of the present invention provides a method for elongating telomeres, the method comprising steps of: providing physical stimulation directly or indirectly to the cells; and culturing a mixture of the cells and a medium for a predetermined time, wherein providing the stimulation directly to the cells comprises applying physical stimulation to a medium containing the cells, and providing the stimulation indirectly to the cells comprises applying physical stimulation to the medium not containing the cells and then mixing the medium and the cells.

Another embodiment of the present invention provides cells having telomeres elongated by physical stimulation.

Technical problems to be achieved by the present invention are not limited to the above-mentioned technical problem, and other technical problems which are not mentioned herein will be clearly understood by those skilled in the art from the following description.

Technical Solution

As a technical means for achieving the above-described technical problem, a method for elongating telomeres according to one aspect of the present invention comprises steps of: providing physical stimulation directly or indirectly to cells; and culturing a mixture of the cells and a medium for a predetermined time, wherein providing the stimulation directly to the cells is applying physical stimulation to a medium containing the cells, and providing the stimulation indirectly to the cells is applying physical stimulation to a medium not containing the cells and then mixing the medium and the cells.

Here, the form of the physical stimulation may be any one selected from among ultrasound, heat, and light.

The step of providing physical stimulation directly or indirectly to cells may be performed by any one method selected from among: a method of mixing the cells and a medium and then providing physical stimulation to the mixture; or a method of providing physical stimulation to a medium and then mixing the medium and the cells; or a method of providing physical stimulation to the cells and then mixing the cells and a medium; or a method of providing physical stimulation to the cells and then mixing the cells and the medium, followed by providing physical stimulation to the mixture; or a method of providing physical stimulation to the medium and then mixing a medium and the cells, followed by providing physical stimulation to the mixture; or a method of providing physical stimulation to each of the cells and a medium and then mixing the cells and the medium; or a method of providing physical stimulation to each of the cells and a medium and then mixing the cells and the medium, followed by providing physical stimulation to the mixture.

The physical stimulation may be ultrasound stimulation, and providing the ultrasound stimulation directly to the cells may be performed at an ultrasound intensity of 0.1 to 3 $W/cm^2$ and a frequency of 20 kHz to 20 MHz for a duration of 0.1 seconds to 20 minutes, and providing the ultrasound stimulation indirectly to the cells may be performed at an ultrasound intensity of 1 to 20 $W/cm^2$ and a frequency of 20 kHz to 20 MHz for a duration of 0.1 seconds to 20 minutes.

The physical stimulation may be heat stimulation at different temperatures, and the heat stimulation may be applied by exposing the cells to a temperature of 40 to 50° C. for 1 to 10 minutes and then exposing the cells to a temperature of 0 to 4° C. for 5 to 10 seconds.

The physical stimulation may be light stimulation, and the light stimulation may be applied by irradiating a pulsed beam, which is selected from laser light or light-emitting diode light and has a wavelength of 300 to 900 nm, for 1 to 10 seconds.

The cells may be selected from the group consisting of mammalian stem cells, progenitor cells, fibroblasts, keratinocytes or organ tissue cells.

The medium may be selected from a culture medium or a differentiation-inducing medium.

The culturing of the mixture may be performed for 1 hour to 10 days.

Expression of one or more of TERT, DKC1, TERF2IP, RFC1, RAD50, TERF1, PINX1, TNKS1BP1, ACD, NBN, HSPA1L, PARP1, PTGES3, SMG6, BLM, XRCC5, XRCC6, ERCC4, PRKDC, TEP1 and β-catenin in the cells after the culturing may increase compared to that before the culturing.

Telomerase activity in the cells after the culturing may increase compared to that before the culturing.

β-galactosidase activity in the cells after the culturing may decrease compared to that before the culturing.

Another aspect of the present invention provides cells having telomeres elongated by physical stimulation.

Here, the form of the physical stimulation may be any one selected from among ultrasound, heat, and light.

The above-described means for solving the problem is merely exemplary and should not be construed as limiting the present invention. In addition to the above-described exemplary embodiments, additional embodiments may exist in the drawings and the detailed description of the invention.

Advantageous Effects

The method for elongating telomeres of cells according to one embodiment of the present invention is simpler and more cost-effective than the above-described conventional methods of elongating telomeres. That is, the conventional methods are methods of administering compounds, and in these methods, a process of synthesizing and purifying these compounds using chemical or biological methods is required, and equipment therefor and materials that must be continuously fed are also required. Chemical synthesis has no specificity and is harmful to the environment, and these shortcomings can be overcome by biosynthesis, but biosynthesis has disadvantages in that the yield is low, mass production and quality maintenance are difficult, the possibility of contamination is high, and thus additional equipment and materials are required to overcome this contamination. In addition, since cells are surrounded by a double lipid membrane, a delivery vehicle capable of delivering these compounds into cells is additionally required depending on the chemical properties of the purified compounds, and in this case, a step of loading the compound into the delivery vehicle is required. In contrast, the method for elongating telomeres of cells according to one embodiment of the present invention exhibits an effect by directly treating the cells with physical stimulation, and thus makes it possible to omit processes such as synthesis, purification, delivery vehicle design and delivery vehicle synthesis. In addition, since the method of the present invention may be carried out as long as there is equipment capable of applying stimulation, it can elongate telomeres at low cost.

In addition, the method for elongating telomeres of cells according to one embodiment of the present invention is superior in terms of time and efficiency compared to the previously disclosed method of elongating telomeres. In the process of synthesizing the telomere-elongating compound according to the conventional technology, raw materials are fed, but not all of them constitute a product, and considerable amounts of materials such as by-products or buffers are discarded. However, in the method of the present invention, there is no such waste, because the method has no process of synthesizing a compound and is a method of applying physical stimulation. In addition, the above-described methods of elongating telomeres the compounds require treating cells with a high concentration of a compound several times or over a long period of time in order to exhibit a sufficient effect, whereas the method for elongating telomeres of cells according to one embodiment of the present invention exhibits an effect by treating cells once with physical stimulation for a short duration of 20 minutes or less.

In addition, the method of elongating telomeres of cells according to one embodiment of the present invention has high safety. That is, the compound may pose additional risks such as toxicity in the metabolic process, and in the above-described conventional technology, the dosage of the compound is considerably high (in the order of mg/kg), waste that burden the environment is generated in the synthesis process, whereas the method according to the present invention does not involve these problems. In addition, the method according to the present invention temporarily induces increased expression of the TERT gene related to telomere elongation by performing ultrasound treatment for a short time. Since continuous expression of the gene is known to be correlated with cancer development, it is expected that, when cells whose telomeres have been elongated by the method of the present invention, in which the effect of increasing the expression of the gene is not long-lasting, are administered for therapeutic purposes or applied to a living body, they will be more safe from the risk of cancer development.

In addition, it was confirmed that the method of elongating telomeres of cells according to one embodiment of the present invention induces cell division and provides an anti-aging effect, in addition to simply elongating telomeres. Thereby, it is expected that the method of the present invention can ameliorate and prevent not only problems caused by shortening of telomeres, but also various aging-related diseases and conditions.

It is to be understood that the effects of the present invention are not limited to the above-described effects, and include all effects that may be deduced from the features described in the detailed description of the invention or the claims.

BEST MODE

Figure 1A:
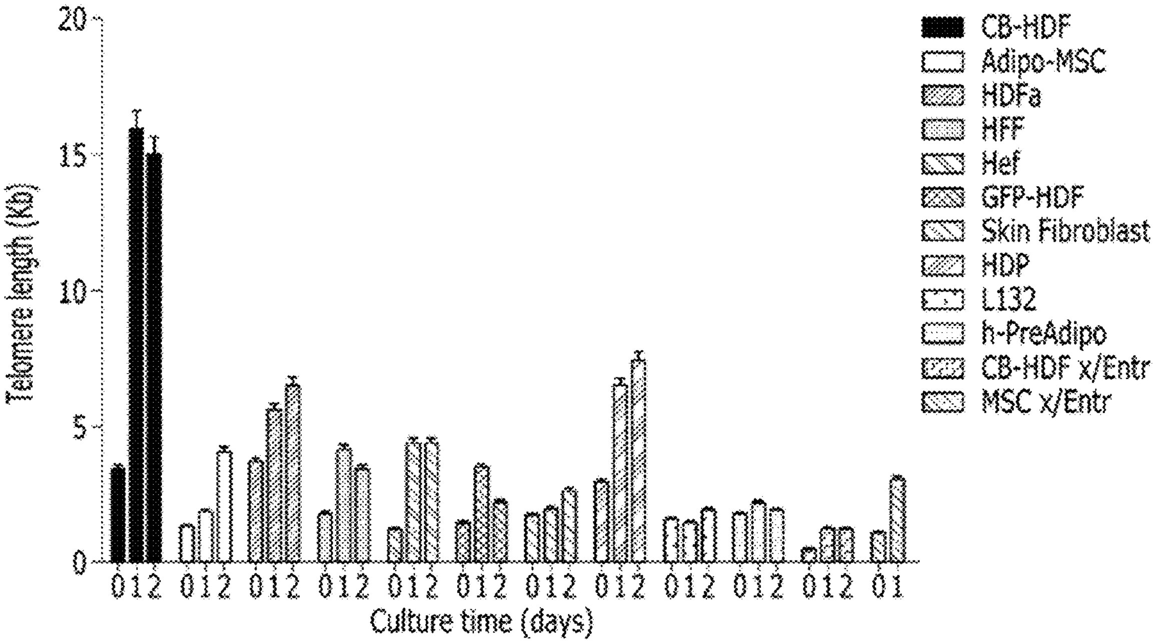
FIG. 1 shows data obtained by analyzing telomere length changes depending on the type of cells after ultrasound treatment and culture according to Example 1 of the present invention.

A method for elongating telomeres according to one aspect of the present invention comprises steps of: providing physical stimulation directly or indirectly to cells; and culturing a mixture of the cells and a medium for a predetermined time, wherein providing the stimulation directly to the cells comprises applying physical stimulation to the medium containing the cells, and providing the stimulation indirectly to the cells comprises applying physical stimulation to the medium not containing the cells and then mixing the medium and the cells.

Here, the form of the physical stimulation may be any one selected from among ultrasound, heat, and light.

The step of providing physical stimulation directly or indirectly to cells may be performed by any one method selected from among: a method of mixing the cells and the medium and then providing physical stimulation to the mixture; or a method of providing physical stimulation to the medium and then mixing the medium and the cells; or a method of providing physical stimulation to the cells and then mixing the cells and the medium; or a method of providing physical stimulation to the cells and then mixing the cells and the medium, followed by providing physical stimulation to the mixture; or a method of providing physical stimulation to the medium and then mixing the medium and the cells, followed by providing physical stimulation to the mixture; or a method of providing physical stimulation to each of the cells and the medium and then mixing the cells and the medium; or a method of providing physical stimulation to each of the cells and the medium and then mixing the cells and the medium, followed by providing physical stimulation to the mixture.

The physical stimulation may be ultrasound stimulation, and providing the ultrasound stimulation directly to the cells may be performed at an ultrasound intensity of 0.1 to 3 $W/cm^2$ and a frequency of 20 kHz to 20 MHz for a duration of 0.1 seconds to 20 minutes, and providing the ultrasound stimulation indirectly to the cells may be performed at an ultrasound intensity of 1 to 20 $W/cm^2$ and a frequency of 20 kHz to 20 MHz for a duration of 0.1 seconds to 20 minutes.

The physical stimulation may be heat stimulation at different temperatures, and the heat stimulation may be applied by exposing the cells to a temperature of 40 to 50° C. for 1 to 10 minutes and then exposing the cells to a temperature of 0 to 4° C. for 5 to 10 seconds.

The physical stimulation may be light stimulation, and the light stimulation may be applied by irradiating a pulsed beam, which is selected from laser light or light-emitting diode light and has a wavelength of 300 to 900 nm, for 1 to 10 seconds.

The cells may be selected from the group consisting of mammalian stem cells, progenitor cells, fibroblasts, keratinocytes or organ tissue cells.

The medium may be selected from a culture medium or a differentiation-inducing medium.

The culturing of the mixture may be performed for 1 hour to 10 days.

Expression of one or more of TERT, TERF2, DKC1, TERF2IP, RFC1, RAD50, TERF1, PINX1, TNKS1BP1, ACD, NBN, HSPA1L, PARP1, PTGES3, SMG6, BLM, XRCC5, XRCC6, ERCC4, PRKDC, TEP1 and β-catenin genes in the cells after the culturing may increase compared to that before the culturing.

Telomerase activity in the cells after the culturing may increase compared to that before the culturing.

β-galactosidase activity in the cells after the culturing may decrease compared to that before the culturing.

Another aspect of the present invention provides cells having telomeres elongated by physical stimulation.

Here, the form of the physical stimulation may be any one selected from among ultrasound, heat, and light.

MODE FOR INVENTION

Hereinafter, the present invention will be described in more detail. However, the present invention may be embodied in various different forms and is not limited by the embodiments described herein, and the scope of the present invention should be defined only by the appended claims.

The terminology used herein is only for the purpose of describing particular embodiments and is not intended to be limiting of the present invention. Singular expressions include plural expressions unless otherwise specified in the context thereof. Throughout the present specification, it is to be understood that when any part is referred to as "comprising" any component, it does not exclude other components, but may further comprise other components, unless otherwise specified.

In addition, the unique name of each gene used under the designation "gene" in the present invention is an officially known gene name, a commonly used name, or the name of a product of the gene, for example, a protein in the case of the gene encoding the protein.

The present inventors previously disclosed in Korean Patent No. 10-1855967 that, when physical stimulation capable of promoting environmental inflow is provided to a mixture of cells and a culture medium and the mixture provided with the physical stimulation is cultured for a predetermined time, reprogrammed cells can be obtained. Here, the direction of reprogramming appears differently depending on the composition of the medium regardless of the type of cell. In the process of analyzing the effect of the cell reprogramming method, it was confirmed that the expression of the gene group related to telomere elongation was also increased by applying physical stimulation. Through further research thereon, it has been found that, unlike the previously disclosed invention described above, telomeres can be elongated by physical stimulation regardless of not only the type of cells tested but also the composition of medium. Based on this finding, it was possible to conclude that telomere elongation was induced by the physical stimulation itself rather than the environmental inflow. Based on this conclusion, a new invention is disclosed.

A method for elongating telomeres according to one aspect of the present invention comprises steps of: providing physical stimulation directly or indirectly to cells; and culturing a mixture of the cells and a medium for a predetermined time, wherein providing the stimulation directly to the cells comprises applying physical stimulation to the medium containing the cells, and providing the stimulation indirectly to the cells comprises applying physical stimulation to the medium not containing the cells and then mixing the medium and the cells.

The form of the physical stimulation may be selected from among low frequency, ultrasound, high frequency, heat, light, electric wave, radio wave, stretch, and compression, and may preferably be any one selected from among ultrasound, heat, and light.

The step of providing physical stimulation directly or indirectly to cells may be performed by any one method selected from among: a method of mixing the cells and the medium and then providing physical stimulation to the mixture; or a method of providing physical stimulation to the medium and then mixing the medium and the cells; or a method of providing physical stimulation to the cells and then mixing the cells and the medium; or a method of providing physical stimulation to the cells and then mixing the cells and the medium, followed by providing physical stimulation to the mixture; or a method of providing physical stimulation to the medium and then mixing the medium and the cells, followed by providing physical stimulation to the mixture; or a method of providing physical stimulation to each of the cells and the medium and then mixing the cells and the medium; or a method of providing physical stimulation to each of the cells and the medium and then mixing the cells and the medium, followed by providing physical stimulation to the mixture. The physical stimulation may be provided directly or indirectly to the cells one or more times, and as the number of times increases, the telomere elongation effect may increase proportionally. When the physical stimulation is provided one or more times as described above, it is preferable to provide a time interval between the provisions so that the cells can recover, and the time interval may be at least 1 day, more preferably at least 2 days.

The physical stimulation may be ultrasound stimulation. Providing the ultrasound stimulation directly to the cells may be performed at an ultrasound intensity of 0.1 to 3 $W/cm^2$ and a frequency of 20 kHz to 20 MHz for a duration of 0.1 seconds to 20 minutes, and providing the ultrasound stimulation indirectly to the cells may be performed at an ultrasound intensity of 1 to 20 $W/cm^2$ and a frequency of 20 kHz to 20 MHz for a duration of 0.1 seconds to 20 minutes. More preferably, providing the ultrasound stimulation directly to the cells may be performed at an ultrasound intensity of 0.5 to 2 $W/cm^2$ and a frequency of 20 kHz to 2 MHz for a duration of 0.1 seconds to 10 minutes, and providing the ultrasound stimulation indirectly to the cells may be performed at an ultrasound intensity of 2 to 10 $W/cm^2$ and a frequency of 20 kHz to 2 MHz for a duration of 1 second to 15 minutes.

The physical stimulation may be heat stimulation at different temperatures, and the heat stimulation may be applied by exposing the cells to a temperature of 40 to 50° C. for 1 to 10 minutes and then exposing the cells to a temperature of 0 to 4° C. for 5 to 10 seconds.

The physical stimulation may be light stimulation, and the light stimulation may be applied by irradiating a pulsed beam, which is selected from laser light or light-emitting diode light and has a wavelength of 300 to 900 nm, for 1 to 10 seconds, preferably 3 to 7 seconds.

It was confirmed that, when the method for elongating telomeres of cells according to one embodiment of the present disclosure was applied to various types of cells, it could elongate telomeres of each type of cells. The cells may be selected from the group consisting of mammalian stem cells, progenitor cells, fibroblasts, keratinocytes, or organ tissue cells. When the cells having elongated telomeres are used for in vivo application, the cells may be either autologous, allogeneic or heterologous. When the cells are heterologous, the cells may be of mammalian origin. In order to reduce the likelihood of immune rejection, the cells are preferably allogeneic cells, most preferably autologous cells.

The medium may be selected from a culture medium or a differentiation-inducing medium. Here, the term "culture medium" refers to a medium optimized for survival of a specific type of cells while maintaining the uniformity of the cells, which is a medium that is used for uniform cell proliferation. On the other hand, the term "differentiation inducing medium" refers to a medium for inducing differentiation of a specific type of cells into another type of cells having other differentiation potentials or functions.

The culturing of the mixture may be performed for 1 hour to 10 days, preferably 1 to 5 days. The reason therefor is as follows. When the above-described physical stimulation is applied to cells, the expression of various genes described later is increased, and in this case, "gene expression" involves transcription, the synthesis and folding of a bioactive substance such as a protein, and the migration of the substance to a necessary position in the cell, and hence it takes time to actually elongate telomeres.

Expression of one or more of TERT, TERF2, DKC1, TERF2IP, RFC1, RAD50, TERF1, PINX1, TNKS1BP1, ACD, NBN, HSPA1L, PARP1, PTGES3, SMG6, BLM, XRCC5, XRCC6, ERCC4, PRKDC, TEP1 and β-catenin genes in the cells after the culturing may increase compared to that before the culturing. TERT (telomerase reverse transcriptase) is a subunit having telomerase catalytic activity, and TERF1 (telomeric repeat binding factor 1) and TERF2 (telomeric repeat binding factor 2) recognize the telomere sequence. It is known that DKC1 (dyskerin pseudouridine synthase 1), RFC1 (replication factor C subunit 1), TNKS1BP1 (tankyrase 1 binding protein 1), NBN (Nibrin), HSPA1L (heat shock protein family A member 1 like), PARP1 (poly ADP-ribose polymerase 1), PTGES3 (prostaglandin E synthase 3), SMG6 (Smg6 homolog, Nonsense mediated mRNA decay factor), XRCC5 (X-ray repair cross complementing 5) and XRCC6 (X-ray repair cross complementing 6) are necessary for stabilization and maintenance of telomeres. It has been reported that TERF2IP (TERF2 interacting protein) and RAD50 (RAD50 homolog, double strand break repair protein) inhibit telomere recombination, and PINX1 (PIN2/TERF1-interacting telomerase inhibitor 1) mediate the accumulation of TERF1 and TERT in the nucleolus, help TRF1 bind to telomerase, and inhibit telomerase activity in the S phase. ACD (adrenocortical dysplasia protein homolog), ERCC4 (excision repair cross-complementation group 4) and PRKDC (protein kinase, DNA-activated, catalytic subunit) are necessary to control the telomere length and for telomere protection, and promote telomere amplification during BLM (bloom syndrome protein) DNA synthesis, and telomerase associated protein 1 (TEP1) forms part of the telomerase complex. β-Catenin is a transcriptional regulator that promotes TERT expression. The method for elongating telomeres according to one aspect of the present invention may be used for various purposes as described below.

Telomerase activity in the cells after the culturing may increase compared to that before the culturing. This increase in telomerase activity may be at least 1.5 times higher after 2 days of the culturing than before the culturing, and as the telomerase activity increases in this manner, the telomere length may increase 1.2 times or more.

β-galactosidase activity in the cells after the culturing may decrease compared to that before the culturing. β-galactosidase is an enzyme that catalyzes the hydrolysis of β-galactoside into monosaccharides, and the lysosomal β-galactosidase is overexpressed and accumulated in senescent cells. As a result, it has been reported that the activity of β-galactosidase in senescent cells is high. It was confirmed that the activity of the enzyme was lowered by the method for elongating telomeres of cells according to one embodiment of the present invention, suggesting that the method has an anti-aging effect.

Another aspect of the present invention provides cells having telomeres elongated by physical stimulation.

Here, the form of the physical stimulation may be any one selected from among ultrasound, heat, and light.

These cells may be produced by the method for elongating telomeres of cells according to one embodiment of the present invention.

The present inventors have found that, when cells are treated with physical stimulation, telomeres of the cells are elongated while the expression of telomerase activity-related genes, such as TERT, TERF2, DKC1, TERF2IP, RFC1, RAD50, TERF1, PINX1, TNKS1BP1, ACD, NBN, HSPA1L, PARP1, PTGES3, SMG6, BLM, XRCC5, XRCC6, ERCC4, PRKDC, TEP1 and β-catenin, in the cells, is increased, and exosomes containing the mRNAs and proteins of these genes are secreted in large amounts. Exosomes containing various factors such as mRNAs and proteins may migrate along the bloodstream and exhibit therapeutic effects by delivering the factors directly to cells. Thus, the method for elongating telomeres of cells according to one aspect of the present invention, the cells according to another aspect of the present invention, and exosomes derived from these cells may be used for therapeutic purposes in a subject in need of the activities of these genes. For example, they may be used for the treatment or amelioration of diseases known to occur due to abnormal telomere maintenance, such as congenital dysphagia, aplastic anemia, Werner syndrome, Bloom syndrome, Ataxia-telangiectasia, Nijmegen breakage syndrome, Ataxia-telangiectasia-like syndrome, and pulmonary fibrosis. In addition, they may be used for the treatment or amelioration of various diseases and conditions caused by cell senescence and loss, for example, various degenerative diseases such as dementia, ataxia, and degeneration of cartilage and bone, autoimmune diseases such as Crohn's disease and chronic obstructive pulmonary disease, hypertension, metabolic syndrome, diabetes, skin aging, pigmentation abnormalities, hair loss, etc. In addition, they may be used for rapid regeneration from various injuries such as burns, wounds, injuries, organ failure, organ loss, and ulcers.

Hereinafter, examples of the present invention will be described in detail so that the present invention can be easily carried out by those skilled in the art. However, the present invention may be embodied in various different forms, and is not limited to the examples described herein.

All cell culture processes in the Examples and Experimental Examples of the present invention were performed at 37° C. under 5% CO2.

Example 1. Induction of Telomere Elongation in Cells by Direct Ultrasound Stimulation Ultrasound stimulation was applied to $1\times10^6$ cells in 1 ml of medium at an ultrasound intensity of 1 $W/cm^2$ and a frequency of 20 KHz for 5 seconds, and the cells were cultured with the same medium in a culture dish for 1 day or more.

Example 2. Induction of Telomere Elongation in Cells by Direct Heat Stimulation $1\times10^6$ cells in 1 ml of hES medium were placed in a 1.5-ml tube and exposed to 50° C. for 5 seconds and then exposed to 0° C. for 10 seconds, and the cells were cultured with the same medium in a culture dish for 1 day or more.

Example 3. Induction of Telomere Elongation in Cells by Direct Light-Emitting Diode Light Stimulation Light-emitting diode light stimulation (1 W, 500 Hz/sec) with a wavelength of 808 nm was applied directly to $1\times10^6$ cells in 1 ml of hES medium for 5 seconds, and the cells were cultured with the same medium in a culture dish for 1 day or more.

Example 4. Induction of Telomere Elongation in Cells by Indirect Ultrasound Stimulation hES medium was treated with ultrasound at 0, 3, 5 and 10 W/cm$^2$ for 10 minutes and then mixed with non-ultrasound-treated cells, followed by 1 day or more of culture.

Example 5. Production of Exosomes Capable of Inducing Cell Telomere Elongation by Ultrasound Stimulation Ultrasound stimulation was applied to $1\times10^6$ cells in 1 ml of medium at an ultrasound intensity of 1 W/cm$^2$ and a frequency of 20 KHz for 5 seconds, and the cells were cultured with the same medium in a culture dish for 1 to 2 days. Next, the conditioned medium was collected and centrifuged at 3000 rpm for 5 minutes to remove cell debris or dead cells, and only the supernatant was collected and filtered through a 0.2-μm filter. The filtrate containing only components having a size of 0.2 μm or less was collected, placed in a 100-kDa filter, and centrifuged at 10,000×g for 30 minutes to remove components having a molecular weight of 100 kDa or less, thus obtaining concentrated exosomes. PBS was added to the 100-kDa filter containing the concentrated exosomes and washed at 10000×g for 5 minutes, and this addition and washing process was repeated twice to remove the medium component from the exosome concentrate, thus obtaining exosomes.

Figure 1B:
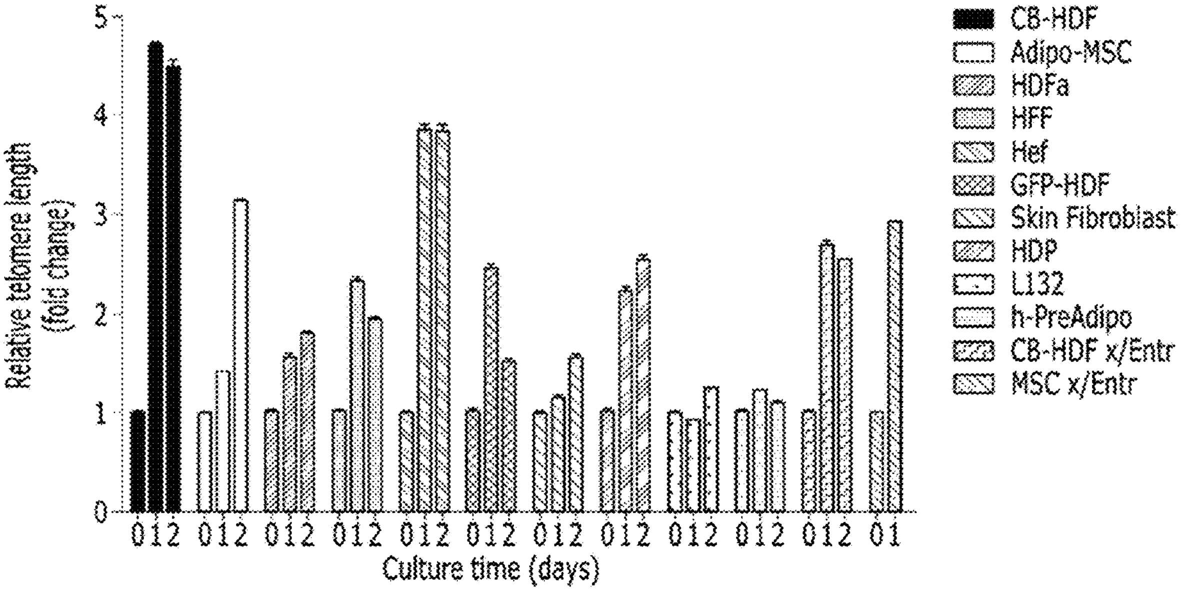

Experimental Example 1. Analysis of Telomere Elongation Effect Depending on Type of Cells In order to compare the effect of Example 1 depending on the type of cells, ultrasound stimulation was added to each of the following types of $1\times10^6$ cells in 1 ml of DMEM medium (fibroblast culture medium) according to the method of Example 1: CB-HDFs (CellBio), Adipo-MSC cells (professor Hwang Dong-Yeon Lab.), HDFa cells (Invitrogen), HFF cells (Cha University), Hef cells (Cha University), GFP-HDF cells (GFP-HNDFs, Angio-proteomie), skin fibroblasts (obtained from a 60-year-old stroke patient sample in compliance with the IRB-approved protocol), HDP cells (CellBio), L132 cells (ATCC), h-PreAdipo cells (ATCC), CB-HDF x/Entr cells, and MSC x/Entr cells (here, CB-HDF x/Entr and MSC x/Entr cells are pluripotent cells derived from CB-HDF and MSC cells, respectively, in human embryonic stem cell culture medium by application of a method of inducing pluripotent cells through ultrasound treatment in the study conducted by the present inventor (Lee et al., An ultra-effective method of generating extramultipotent cells from human fibroblasts by ultrasound, Biomaterials, 2017.)). Then, the cells were cultured for 0, 1 and 2 days, and the telomere lengths in the cells were analyzed according to a qPCR method using a kit (Absolute Human Telomere Length Quantification qPCR Assay Kit, Cat No. 8918, ScienCell). As a result, as shown in FIG. 1A, FIG. 1B and Table 1 below, it was confirmed that telomeres in all the types of cells were elongated.

TABLE 1

| | Change (fold) in telomere length relative to control | |
|---|---|---|
| Type of cell | Absolute value (kb) | Relative value (fold) |
| CB-HDF | 12.04 | 4.47 |
| MSC | 1.65 | 2.28 |
| HDFa | 2.36 | 1.79 |
| HFF | 2.00 | 2.14 |
| Hef | 3.22 | 3.80 |
| GFP-HDF | 2.36 | 1.79 |
| Skin Fibroblast | 0.57 | 1.34 |
| HDP | 4.05 | 2.40 |
| L132 | 1.30 | 1.54 |
| h-PreAdipo | 3.15 | 2.44 |
| CB-HDF x/Entr | 0.85 | 1.26 |
| MSC x/Entr | 1.82 | 2.93 |

Figure 2A:
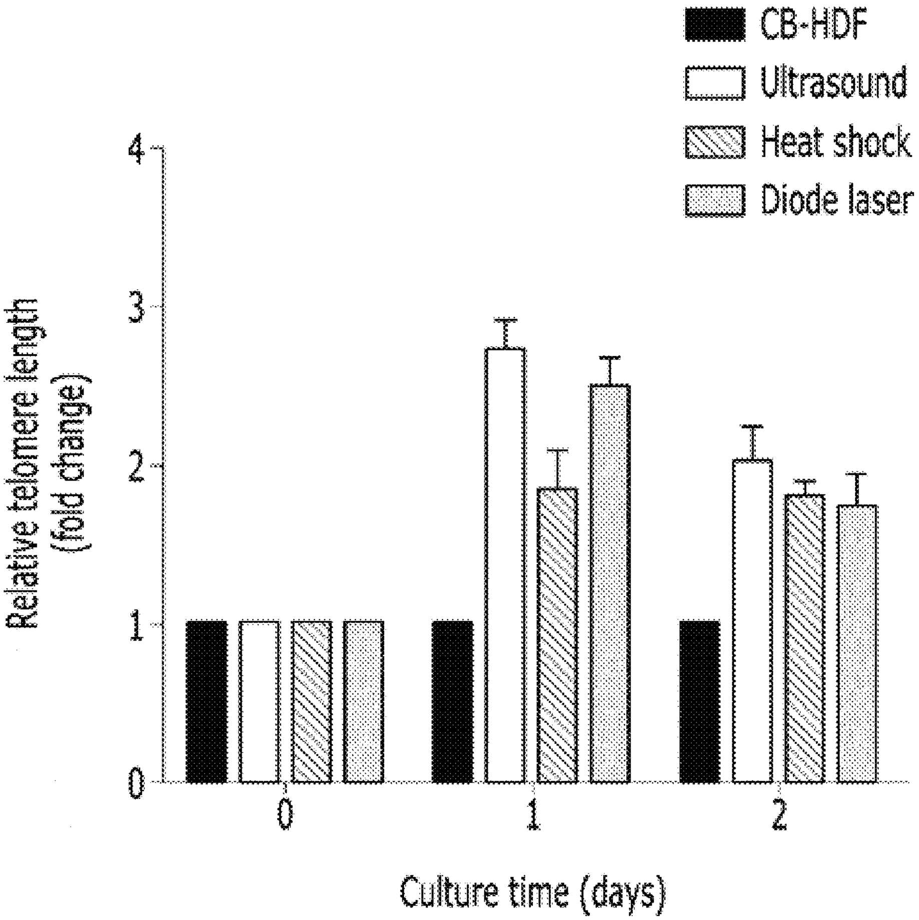
FIG. 2A and FIG. 2B shows data obtained by analyzing telomere length changes caused by each physical stimulation treatment after ultrasound stimulation treatment and culture according to Example 1 of the present invention, heat stimulation treatment and culture according to Example 2, and light-emitting diode laser light stimulation treatment and culture according to Example 3.
Figure 2B:
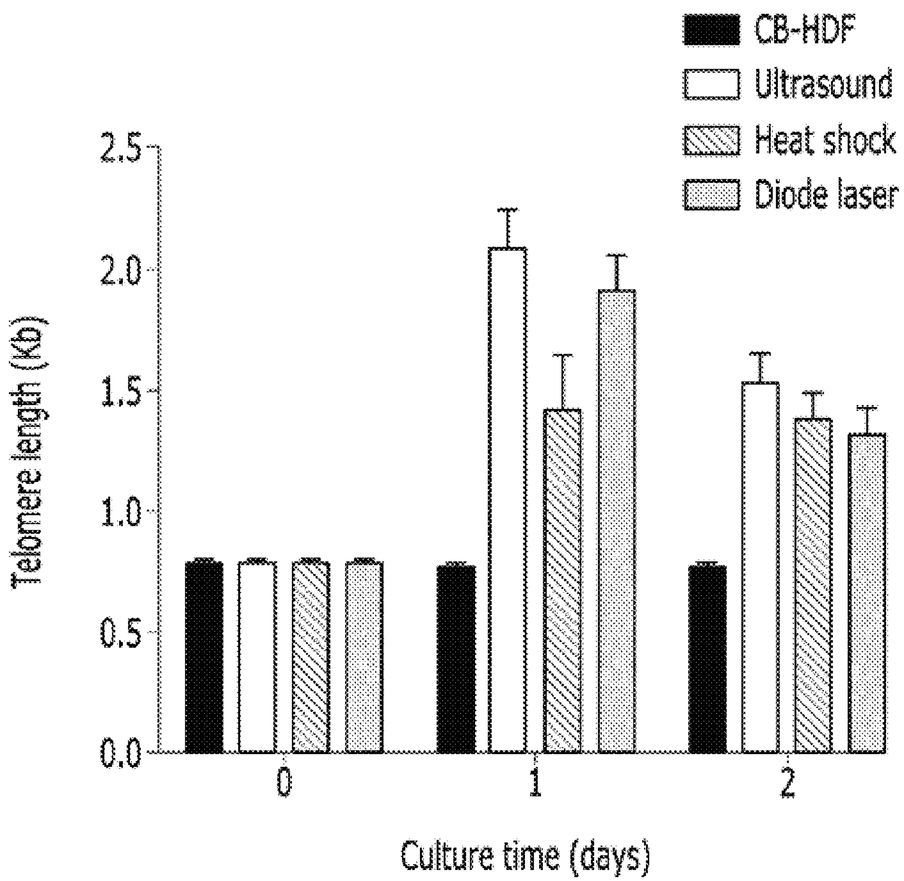

Experimental Example 2. Analysis of Telomere Elongation Effect Depending on Kind of Physical Stimulation To analyze the effect of physical stimulation on telomere analysis depending on the kind of physical stimulation, each physical stimulation was added to CB-HDFs in human embryonic stem cell culture medium according to the methods of Examples 1 to 3, and then the cells were cultured for 0, 1 and 2 days, and the telomere length in the cells was analyzed according to a qPCR method. As a result, as shown in FIG. 2A and FIG. 2B, it was confirmed that ultrasound, heat and light stimuli all elongated telomeres.

Figure 3A:
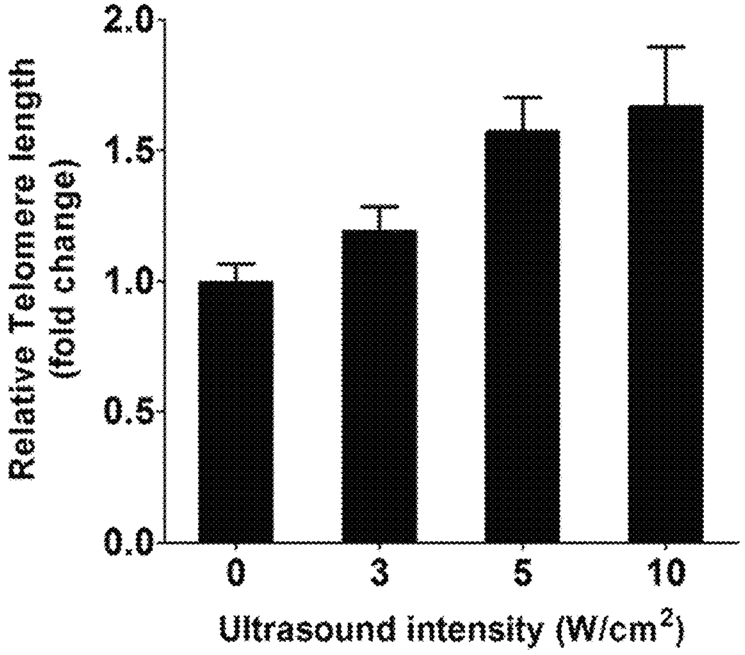
FIG. 3A and FIG. 3B shows data obtained by analyzing telomere length changes after indirect ultrasound stimulation treatment and culture according to Example 5 of the present invention.
Figure 3B:
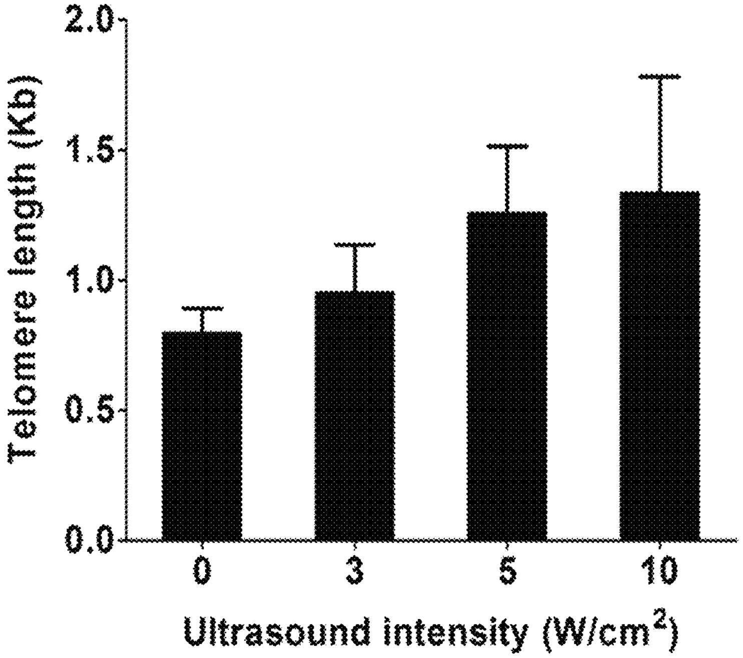

Experimental Example 3. Analysis of Telomere Elongation Effect of Indirect Ultrasound Stimulation In order to examine whether telomeres are elongated even by indirect physical stimulation, not by direct physical stimulation, indirect ultrasound stimulation was applied to CB-HDFs according to the method of Example 2, and then the cells were cultured for 1 day, and the telomere length in the cells were analyzed according to a qPCR method. As a result, as shown in FIG. 3A and FIG. 3B, it was confirmed that the effect on telomere elongation was great in proportion to the intensity of the ultrasound used.

Figure 4A:
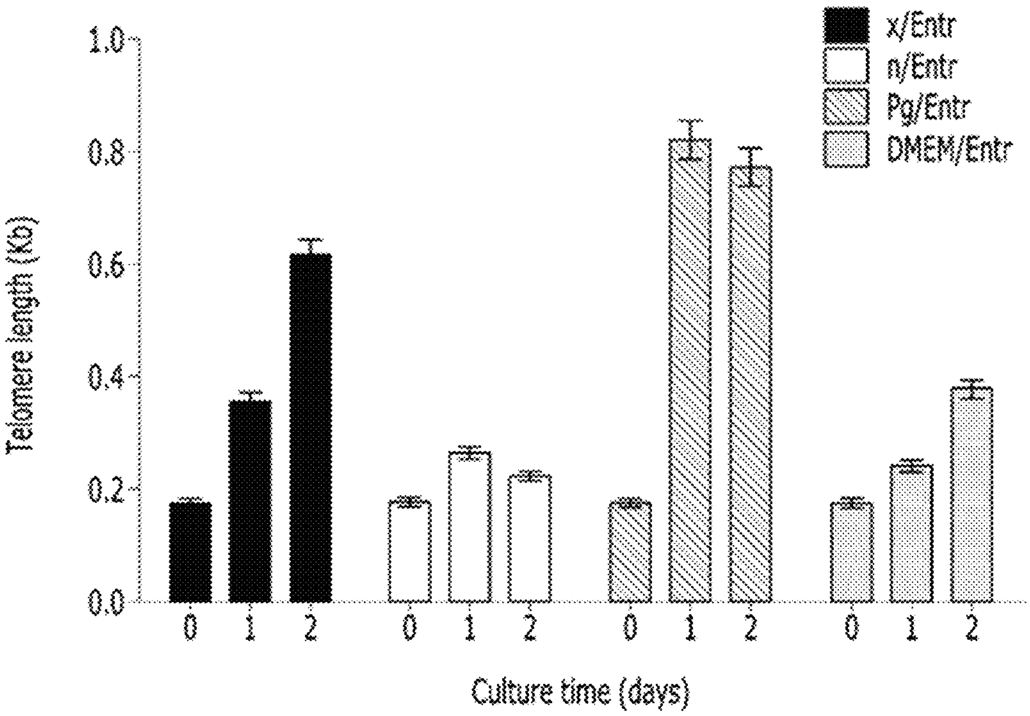
FIG. 4A and FIG. 4B shows data obtained by analyzing telomere length changes depending on the kind of medium after ultrasound treatment and culture according to Example 1 of the present invention.
Figure 4B:
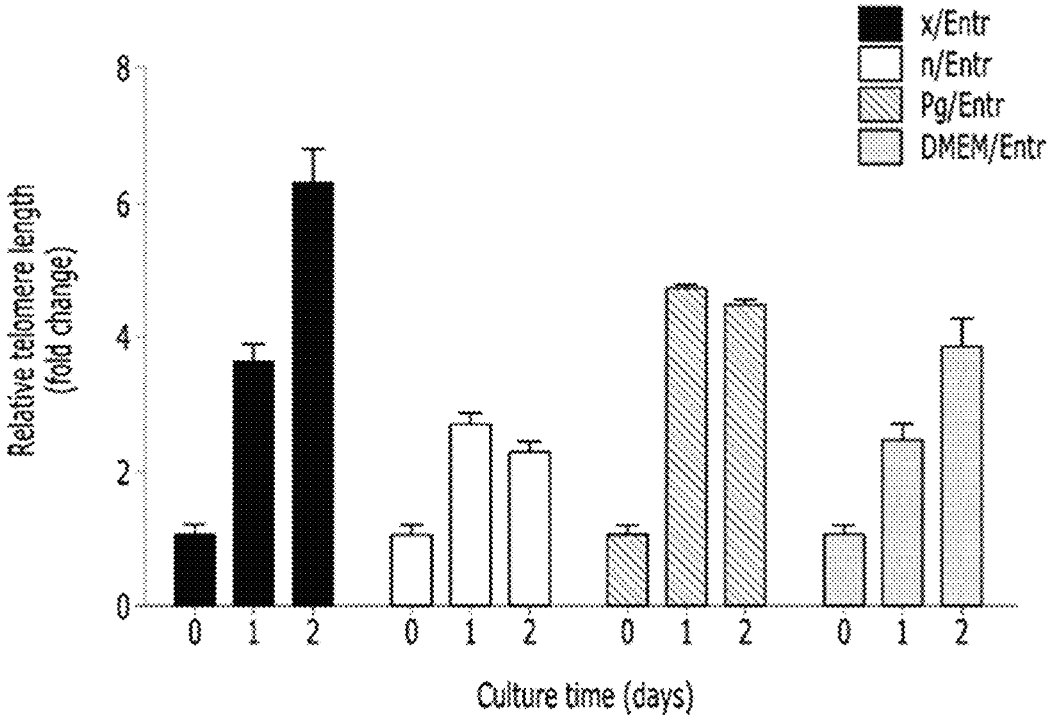

Experimental Example 4. Analysis of Telomere Elongation Effect After Ultrasound Treatment Depending on Medium Composition In order to compare the effect of Example 1 depending on the composition of medium, ultrasound was applied to $1\times10^6$ CB-HDFs in 1 ml of each of human embryonic stem cell culture medium, neural stem cell culture medium, primary germ cell culture medium and DMEM medium according to the method of Example 1, and then the cells were cultured for 0, 1 and 2 days, and the telomere length in the cells was analyzed according to a qPCR method. As a result, as shown in FIG. 4A and FIG. 4B, it was confirmed that telomeres were elongated regardless of the composition of medium.

Figure 5A:
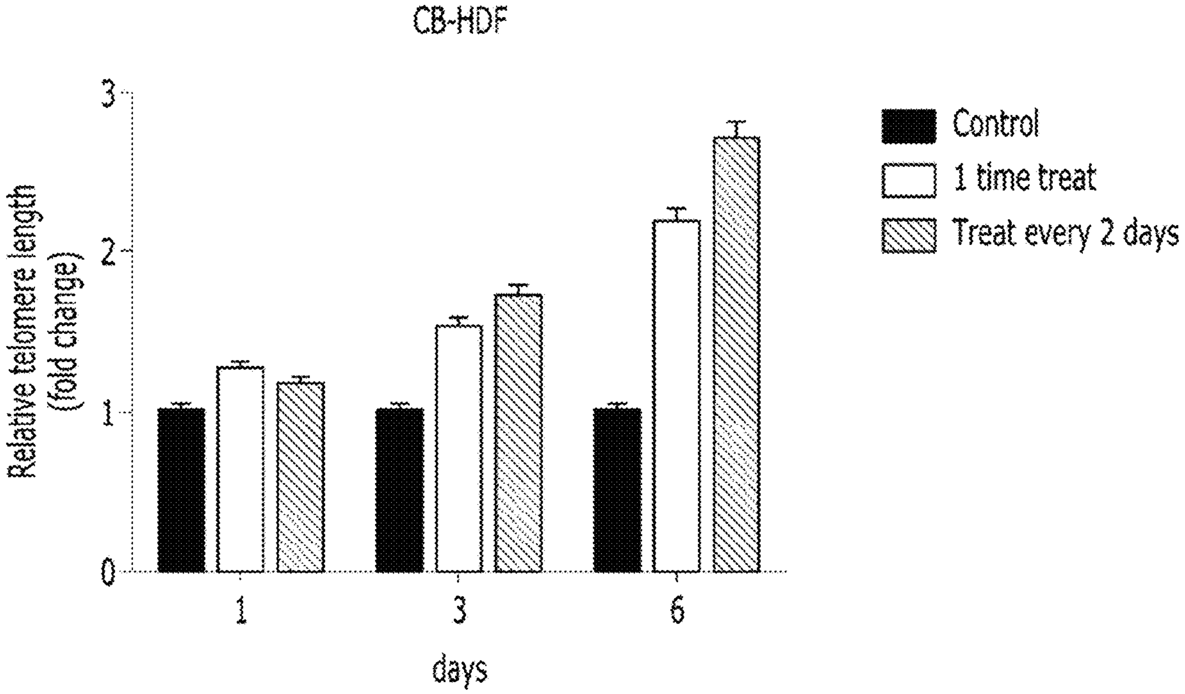
FIG. 5A and FIG. 5B shows data obtained by analyzing telomere length changes depending on the number of ultrasound treatments after ultrasound treatment and culture according to Example 1 of the present invention.
Figure 5B:
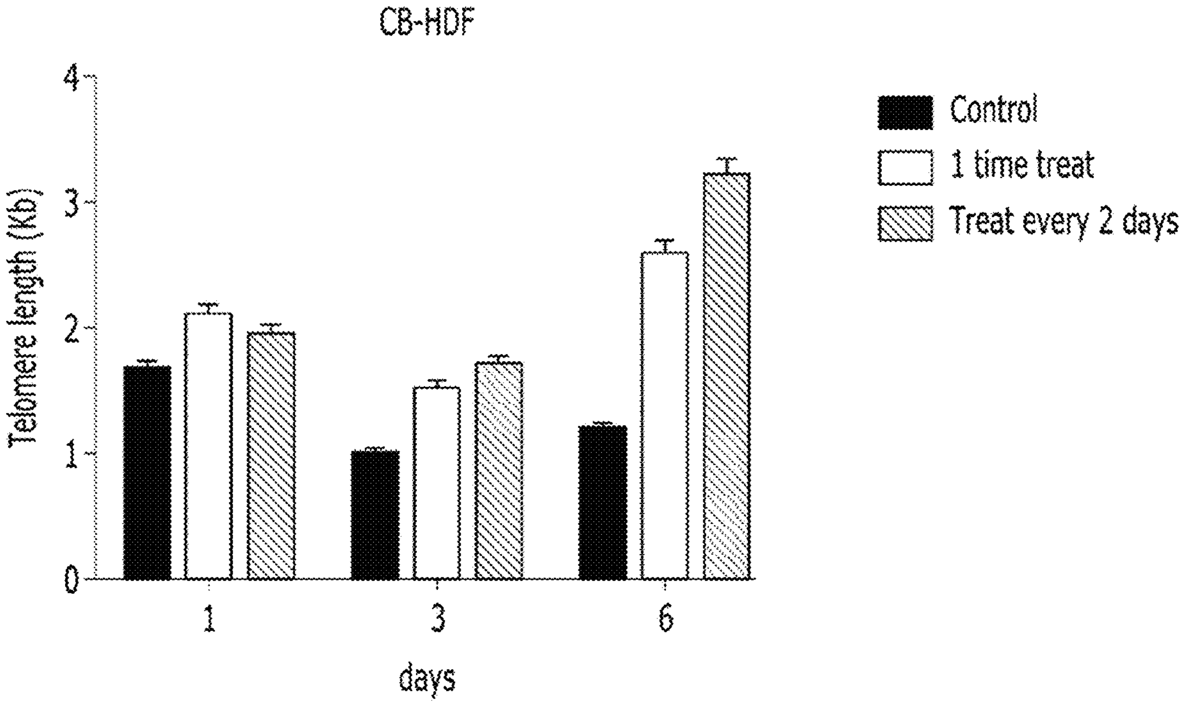

Experimental Example 5. Analysis of Telomere Elongation Effect Depending on Number of Ultrasound Treatments In order to examine whether a difference appears when the ultrasound according to Example 1 is repeated, ultrasound stimulation was applied to 1×$10^6$ CB-HDFs in 1 ml of DMEM medium according to the method of Example 1, and the cells were cultured for 1, 3 and 6 days. In this case, the ultrasound stimulation was applied one time or applied every 2 days. The telomere length in the cells was analyzed according to a qPCR method. As a result, as shown in FIG. 5A and FIG. 5B, it was confirmed that the telomere length increased regardless of the number of ultrasound treatments, and as the number of ultrasound treatments increased, the increment in the telomere length compared to the control not treated with ultrasound increased.

Figure 6:
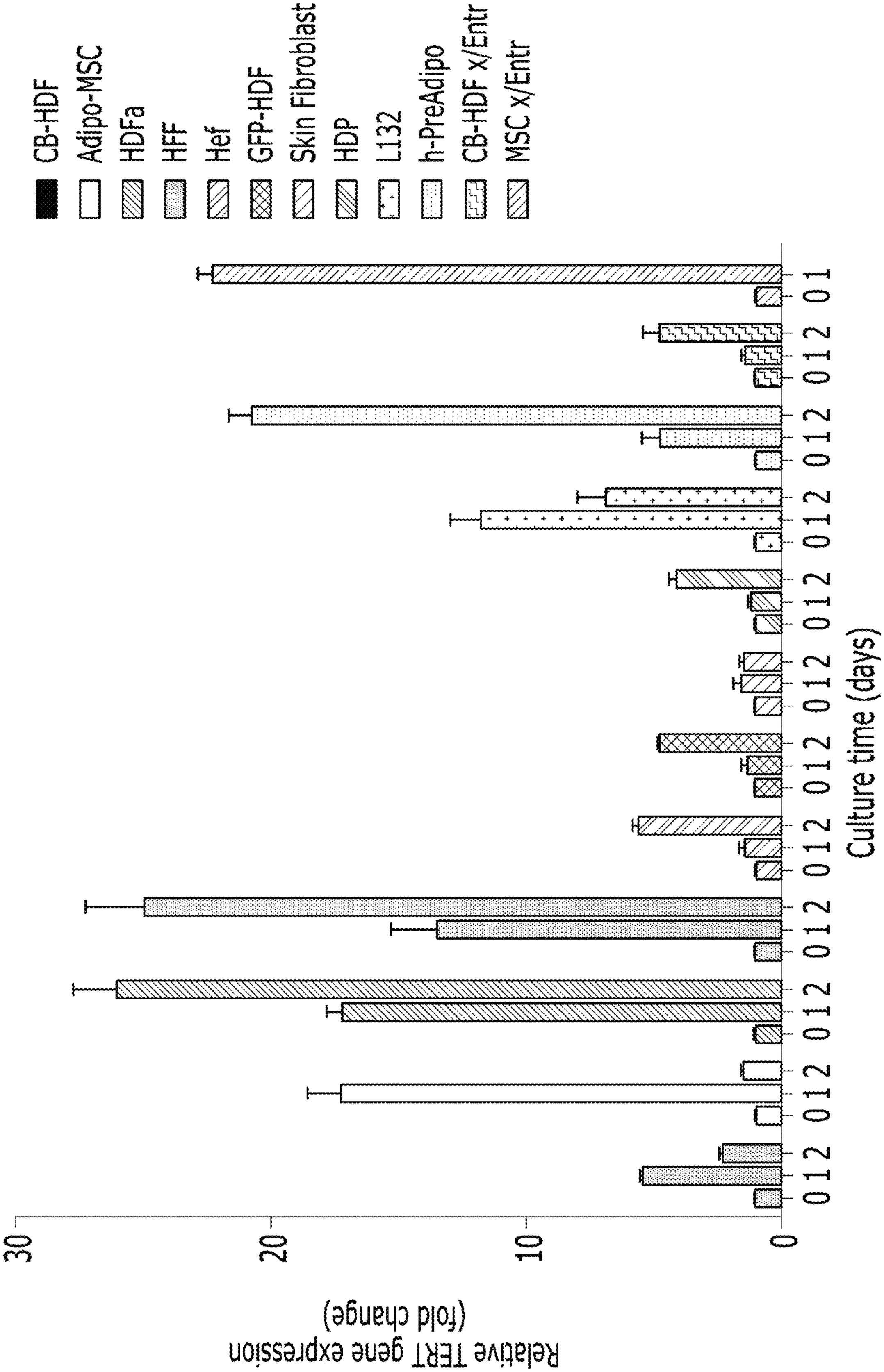
FIG. 6 shows data obtained by analyzing changes in TERT gene expression depending on the type of cells after ultrasound treatment and culture of the cells according to Example 1 of the present invention.
Figure 7:
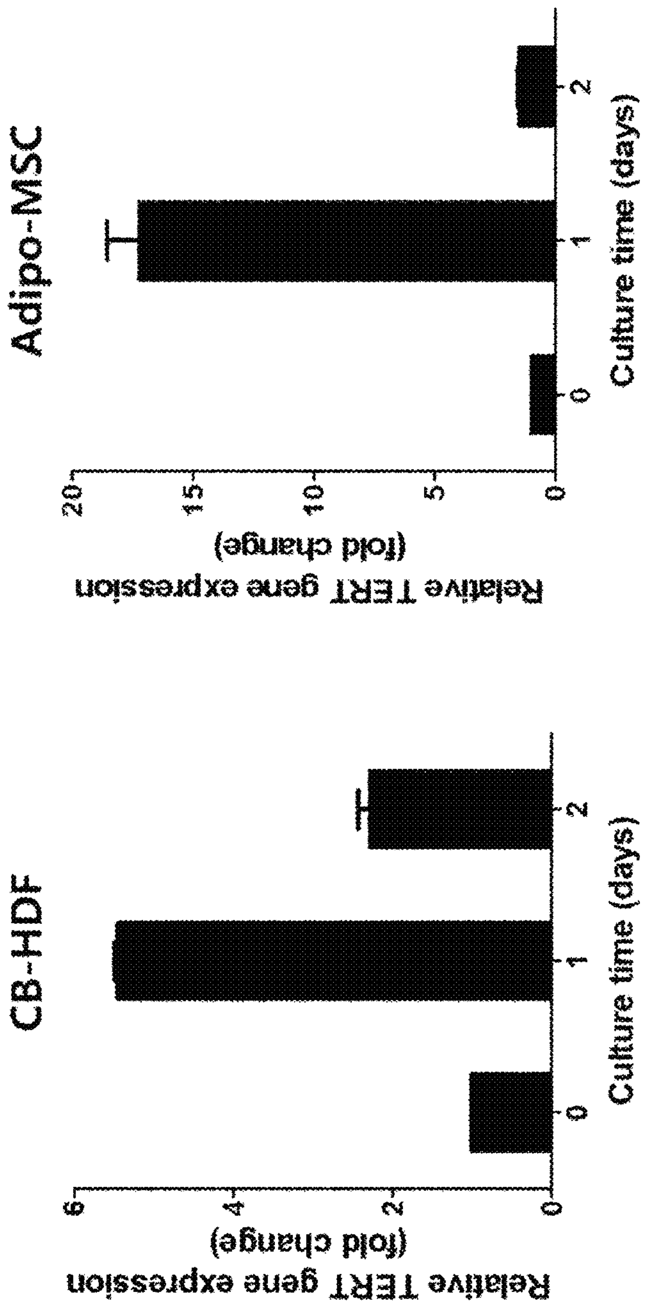
FIG. 7 shows data obtained by analyzing changes in TERT gene expression in CB-HDFs and Adipo-MSC cells after ultrasound treatment and culture of the CB-HDFs and Adipo-MSC cells according to Example 1 of the present invention.

Experimental Example 6. Analysis of TERT Gene Expression after Ultrasound Treatment Depending on Type of Cells In order to examine whether the method of Example 1 shows a difference in the expression level of TERT gene depending on the type of cells, ultrasound stimulation was applied to each of the following types of 1×$10^6$ cells according to the method of Example 1: CB-HDFs, Adipo-MSC cells, HDF cells, HFF cells, Hef cells, GFP-HDF cells, skin fibroblasts, HDP cells, L132 cells, h-PreAdipo cells, CB-HDF x/Entr cells and MSC x/Entr cells. Then, the cells were cultured for 0, 1 and 2 days, and changes in TERT gene expression in the cells were analyzed according to a qPCR method. As a result, as shown in FIG. 6 and Table 2 below, it was confirmed that the expression levels of TERT in all the types of cells increased. In addition, as shown in FIG. 7, it was shown that the expression levels of TERT in CB-HDFs and Adipo-MSC cells significantly increased on day 1 of culture after ultrasound treatment and then decreased again on day 2. That is, since continuous expression of TERT has a risk of development of cancer, etc., it is expected that temporary expression of TERT may ameliorate aging-related conditions caused by telomere shortening while reducing this risk.

TABLE 2

| Type of cell | Change (fold) in TERT gene expression relative to control |
|---|---|
| CB-HDF | 5.4 |
| MSC | 19.46 |
| HDFa | 21.61 |
| HFF | 16.81 |
| Hef | 3.50 |
| GFP-HDF | 3.05 |
| Skin Fibroblast | 1.53 |
| HDP | 2.66 |
| L132 | 6.88 |
| h-PreAdipo | 11.92 |
| CB-HDF x/Entr | 3.08 |
| MSC x/Entr | 22.20 |

Figure 8:
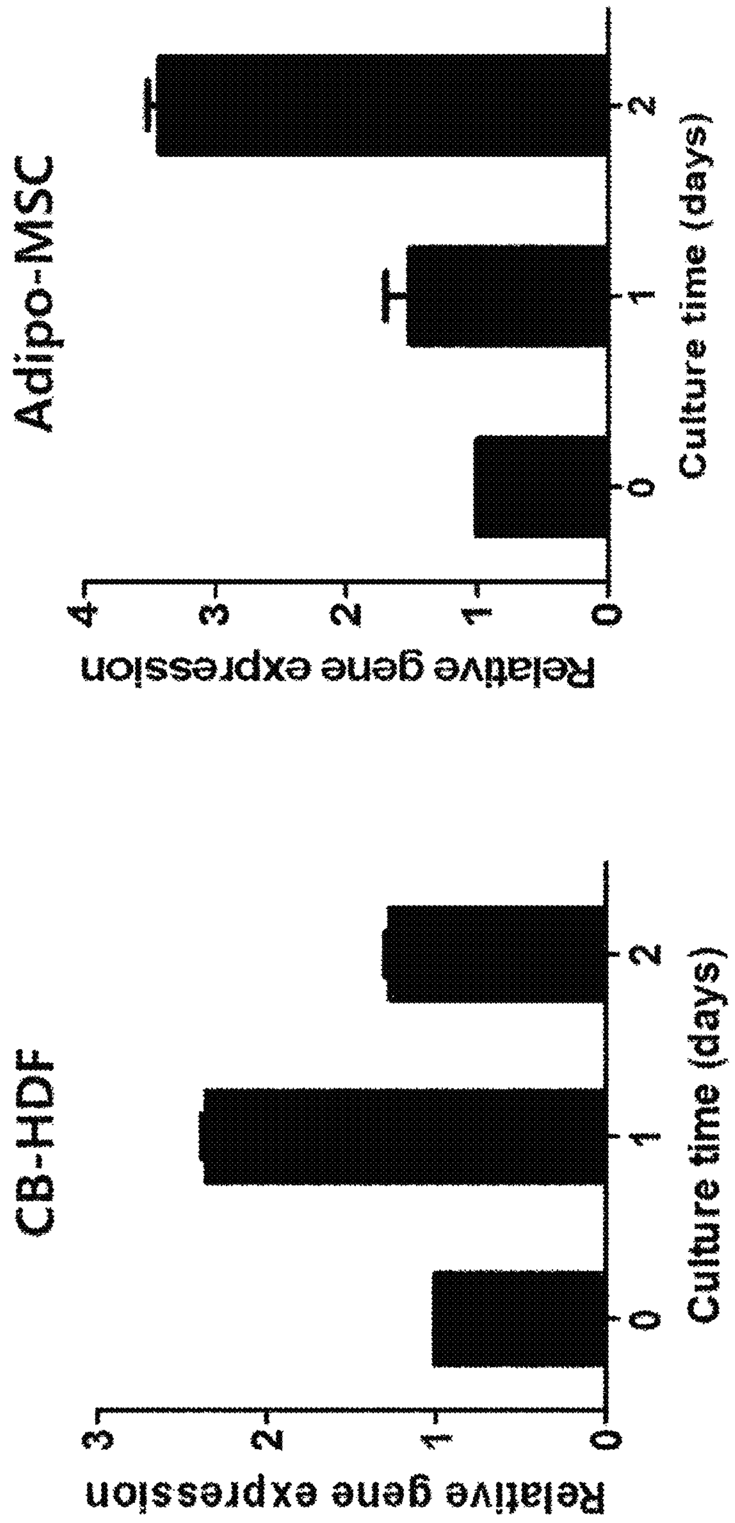
FIG. 8 shows data obtained by analyzing changes in β-catenin gene expression in CB-HDFs and Adipo-MSC cells after ultrasound treatment and culture of the CB-HDFs and Adipo-MSC cells according to Example 1 of the present invention.

Experimental Example 7. Analysis of Change in Intracellular β-Catenin Gene Expression by Ultrasound Treatment In order to examine how the telomere elongation method according to Example 1 affects the β-catenin gene which is a transcriptional activator of TERT, ultrasound stimulation was applied to 1×$10^6$ CB-HDFs in 1 ml of DMEM medium and 1×$10^6$Adipo-MSC cells in 1 ml of DMEM medium according to the method of Example 1, and then the cells were cultured for 0, 1 and 2 days, and changes in β-catenin gene expression in the cells were analyzed according to a qPCR method. As a result, as shown in FIG. 8, the expression levels of β-catenin increased in the two types of cells tested all increased.

Figure 9:
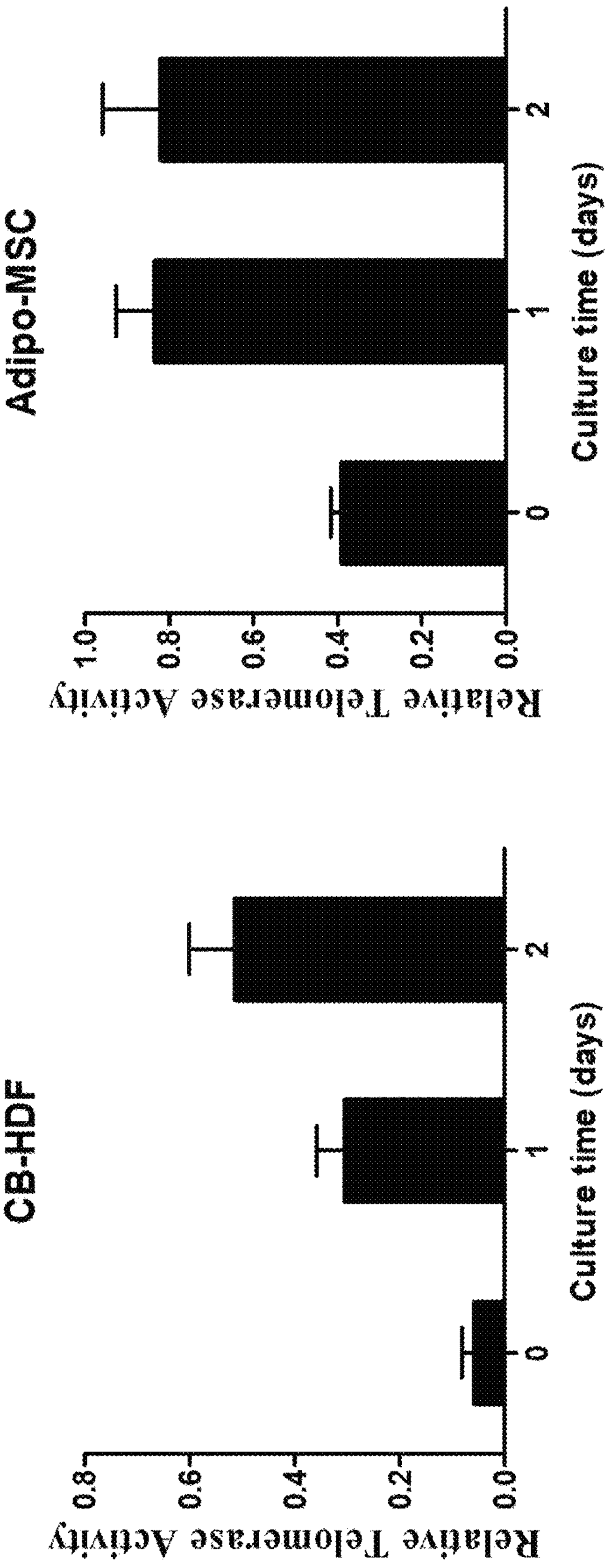
FIG. 9 shows data obtained by analyzing telomerase activity changes in CB-HDFs and Adipo-MSC cells after ultrasound treatment and culture of the CB-HDFs and Adipo-MSC cells according to Example 1 of the present invention.

Experimental Example 8. Analysis of Change in Intracellular Telomerase Activity by Ultrasound Treatment In order to examine how the telomere elongation method according to Example 1 affects telomerase activity, ultrasound stimulation was applied to 1×$10^6$CB-HDFs in 1 ml of DMEM medium and 1×$10^6$Adipo-MSC cells in 1 ml of DMEM medium according to the method of Example 1, and then the cells were cultured for 0, 1 and 2 days, and telomerase activities in the cells were analyzed by Sciencell's Telomerase Activity Quantification qPCR Assay kit (TAQ). As a result, as shown in FIG. 9, it was confirmed that telomerase activities in the two types of cells tested all increased.

Figure 10A:
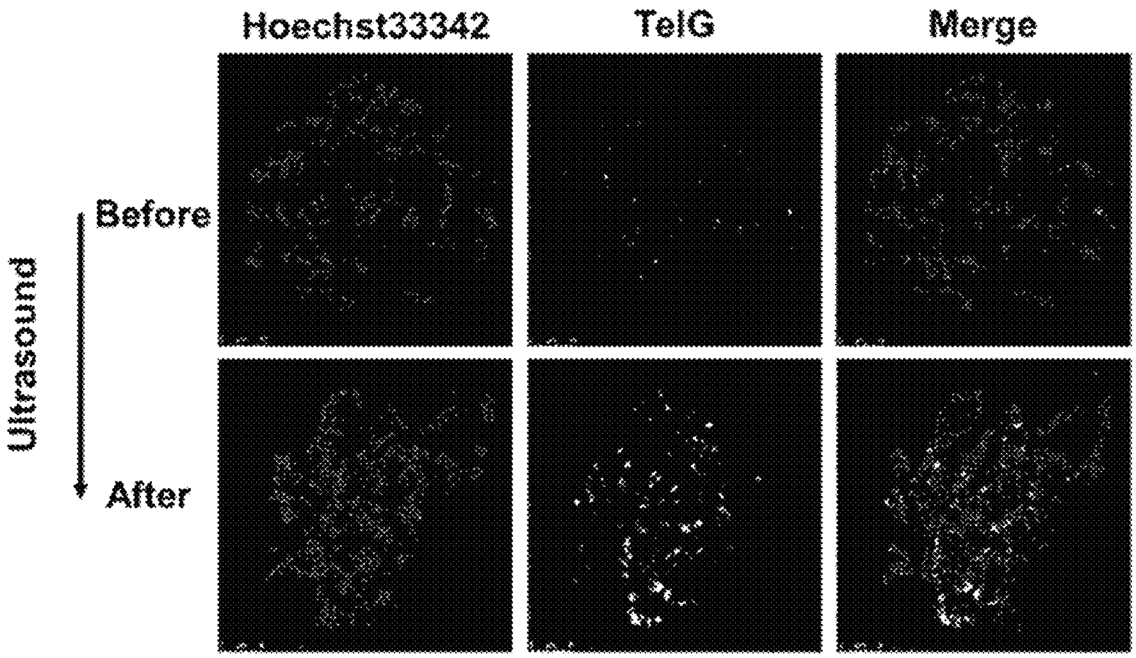
FIG. 10A and FIG. 10B shows data obtained by performing FISH analysis of telomeres in CB-HDFs and Adipo-MSC cells after ultrasound treatment and culture according to Example 1 of the present invention.
Figure 10B:
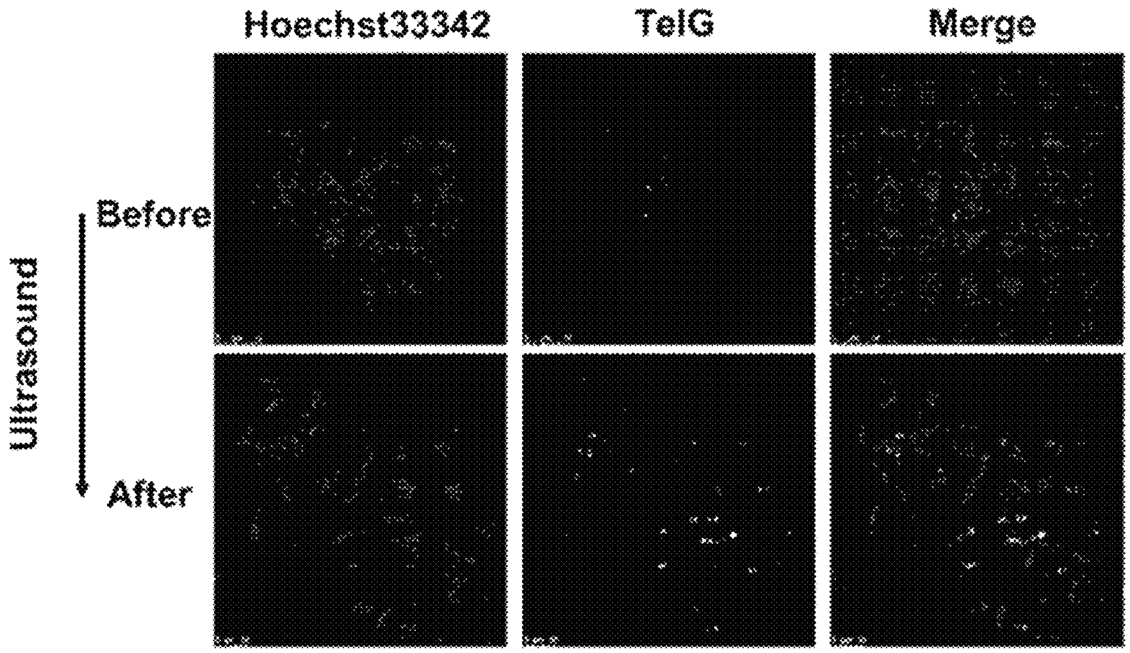

Experimental Example 9. FISH Analysis of Telomeres in Ultrasound-Treated Cells In order to further confirm that telomere elongation is induced by the telomere elongation method according to Example 1, ultrasound stimulation was applied to 1×$10^6$ CB-HDFs in 1 ml of DMEM medium and 1×$10^6$Adipo-MSC cells in 1 ml of DMEM medium according to the method of Example 1, and then the cells were cultured for 1 day. Then, fluorescence in situ hybridization (FISH) analysis was performed using a TelG telomere probe (TTAGGGTTAGGGTTAGGG), and fluorescent signals were analyzed with a confocal microscope. At this time, the cells were counterstained with Hoechst 33342. As a result, as shown in FIG. 10A and FIG. 10B, it was confirmed that the amounts of telomeres in the two types of cells tested all increased.

Figure 11:
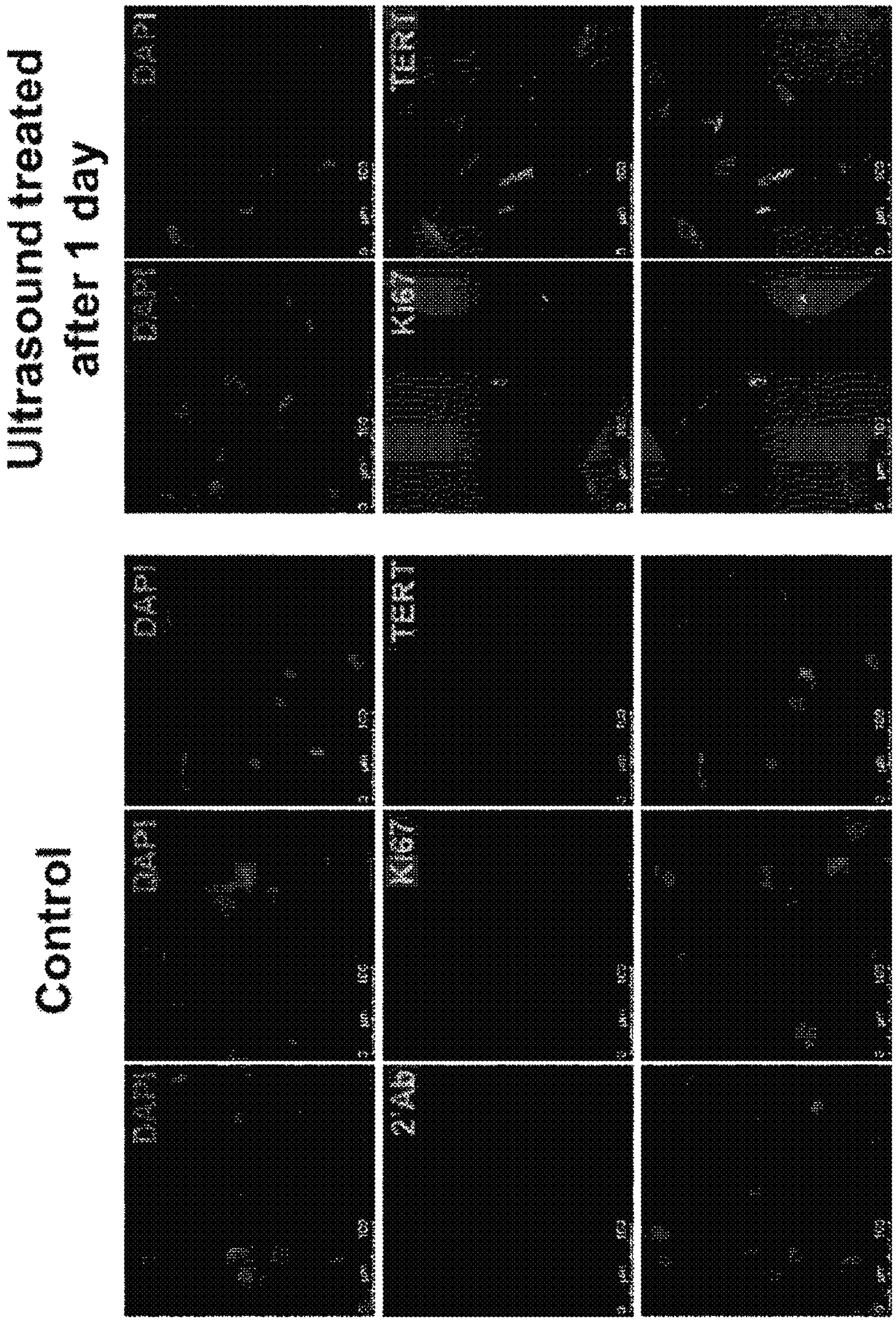
FIG. 11 shows data obtained by performing fluorescence staining for TERT and Ki67 in CB-HDFs after ultrasound treatment and culture of the CB-HDFs according to Example 1 of the present invention.

Experimental Example 10. Cell Immunofluorescence Staining for Ki67 and TERT in Ultrasound-Treated Cells In order to confirm whether TERT gene expression induced by the telomere extension method according to Example 1 leads to an increase in protein expression, ultrasound stimulation was applied to 1×$10^6$ CB-HDFs in 1 ml of DMEM medium according to the method of Example 1, and the cells were cultured for 1 day, and then fluorescence-stained using anti-Ki67 and anti-TERT antibodies and observed with a confocal microscope. As a result, as shown in FIG. 11, it was confirmed that, when the cells were treated with ultrasound, expression of the telomere-related TERT protein increased and expression of the cell division marker Ki67 protein also increased.

Figure 12A:
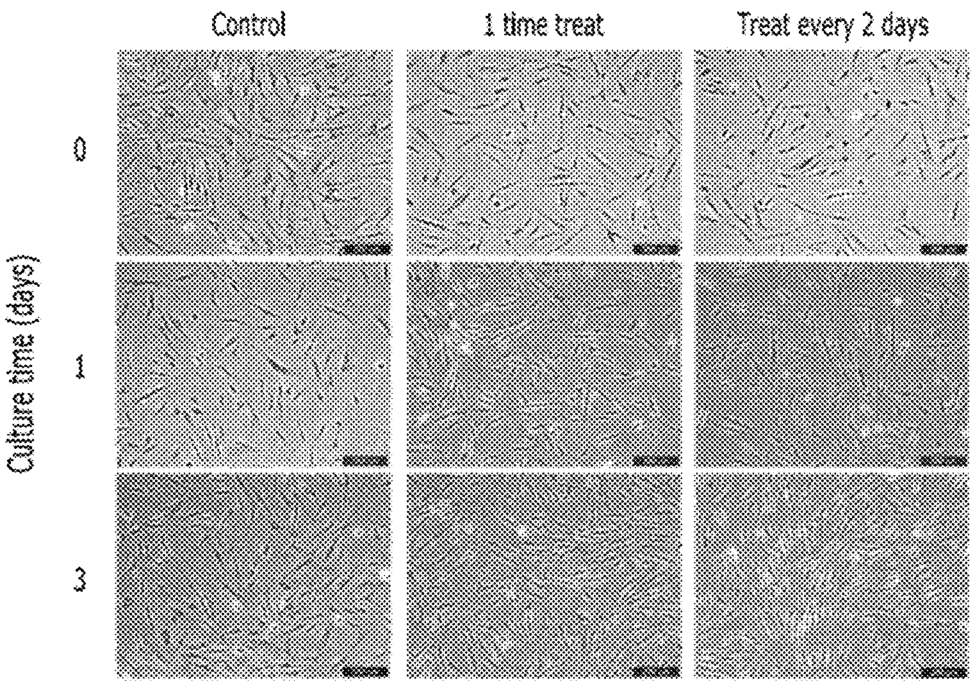
FIG. 12A and FIG. 12B shows data obtained by analyzing senescence-related β-galactosidase activity in CB-HDFs after ultrasound treatment and culture of the CB-HDFs according to Example 1 of the present invention.
Figure 12B:
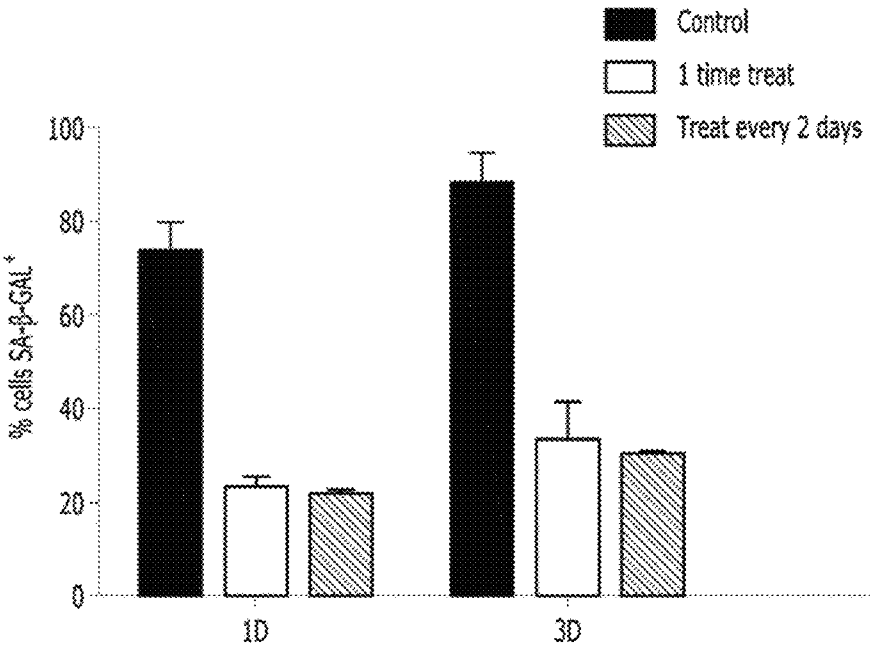

Experimental Example 11. Analysis of Senescence-Related β-Galactosidase Activity In order to examine how the above-described changes caused by the telomere elongation method according to Example 1 affects cell senescence, ultrasound stimulation was applied to 1×$10^6$CB-HDFs in 1 ml of DMEM medium according to the method of Example 1, and the cells were cultured for 1 day and 3 days. Then, a test for β-galactosidase activity known to have a correlation with intracellular senescence was performed using X-gal, followed by analysis with a phase contrast microscope. At this time, the ultrasound treatment was performed one time or performed every 2 days. As a result, as shown in FIG. 12A and FIG. 12B, it could be confirmed that β-galactosidase activity decreased, suggesting that the method for elongating telomeres according to the present invention has an anti-senescence effect.

Experimental Example 12. Analysis of Changes in Gene Expression in Cells Through RNA-Sea Analysis of Genes in Exosomes Secreted from Cells In Korean Patent No. 10-1855967 which is the previous invention of the present inventors, changes in gene expression in cells and exosome secretion from cells could be induced by ultrasound treatment. Since secreted exosomes contain gene products expressed in cells, changes in gene expression in cells whose telomeres have been elongated by the method of Example 1 were analyzed through gene expression in exosomes secreted from the cells. As a result of RNA-seq, as shown in Table 3 below, it was confirmed that expression of telomerase activity-related genes and genes associated with telomere maintenance and protection in the exosomes secreted from the cells of the experimental group increased.

TABLE 3

| | | Read count | |
|---|---|---|---|
| | Genes | HDF.Exo | x.Exo |
| Telomerase activity-related genes | TNKS1BP1 | 0 | 17 |
| | PINX1 | 0 | 15 |
| | TERF1 | 0 | 7 |
| | RAD50 | 0 | 6 |
| | RFC1 | 0 | 5 |
| | TERF2IP | 0 | 5 |
| | DKC1 | 0 | 3 |
| | TERF2 | 0 | 3 |
| | TERT | 0 | 3 |
| Genes associated with telomere maintenance and protection | TEP1 | 0 | 94 |
| | PRKDC | 0 | 33 |
| | ERCC4 | 0 | 23 |
| | XRCC5 | 0 | 19 |
| | XRCC6 | 0 | 18 |
| | TNKS1BP1 | 0 | 17 |
| | PINX1 | 0 | 15 |
| | BLM | 0 | 11 |
| | SMG6 | 0 | 11 |
| | PTGES3 | 0 | 10 |
| | PARP1 | 0 | 7 |
| | TERF1 | 0 | 7 |
| | RAD50 | 0 | 6 |
| | RFC1 | 0 | 5 |
| | TERF2IP | 0 | 5 |
| | HSPA1L | 0 | 4 |
| | NBN | 0 | 4 |
| | ACD | 0 | 3 |
| | DKC1 | 0 | 3 |

TABLE 3-continued

| | | Read count | |
|---|---|---|---|
| | Genes | HDF.Exo | x.Exo |
| | TERF2 | 0 | 3 |
| | TERT | 0 | 3 |

The above description of the present invention is exemplary, and those of ordinary skill in the art will appreciate that the present invention can be easily modified into other specific forms without departing from the technical spirit or essential characteristics of the present invention. Therefore, it should be understood that the embodiments described above are exemplary in all aspects and are not restrictive. For example, each component described to be of a single type can be implemented in a distributed manner. Likewise, components described to be distributed can be implemented in a combined manner.

The scope of the present invention is defined by the appended claims, and it shall be understood that all modifications and alterations conceived from the meaning and scope of the claims and equivalents thereto are included in the scope of the present invention.

The invention claimed is:

1. A method for elongating telomeres of cells, the method comprising:

providing physical stimulation directly or indirectly to the cells; and culturing a mixture of the cells and a first medium for a predetermined time, wherein the providing the stimulation directly to the cells is applying the physical stimulation to a second medium containing the cells, and the providing the stimulation indirectly to the cells is applying the physical stimulation to the first medium not containing cells and then mixing the first medium and the cells, wherein a form of the physical stimulation is direct heat, wherein the direct heat stimulation is applied by exposing the cells to a temperature of 40 to 50° C. for 1 to 10 seconds and then exposing the cells to a temperature of 0 to 4° C. for 5 to 10 seconds, and wherein the cells are mammalian cells selected from the group consisting of stem cells, progenitor cells, fibroblasts, keratinocytes or organ tissue cells.

2. The method of claim 1, wherein the first medium and the second medium are selected from among a culture medium or a differentiation-inducing medium.

3. The method of claim 1, wherein the culturing of the mixture is performed for 1 hour to 10 days.

4. The method of claim 1, wherein expression of one or more of TERT, TERF2, DKC1, TERF2IP, RFC1, RAD50, TERF1, PINX1, TNKS1BP1, ACD, NBN, HSPA1L, PARP1, PTGES3, SMG6, BLM, XRCC5, XRCC6, ERCC4, PRKDC, TEP1 and β-catenin genes in the cells after the culturing increases compared to that before the culturing.

5. The method of claim 1, wherein telomerase activity in the cells after the culturing increases compared to that before the culturing.

6. The method of claim 1, wherein β-galactosidase activity in the cells after the culturing decreases compared to that before the culturing.

* * * * *